(12) United States Patent
Anderson et al.

(10) Patent No.: US 11,580,390 B2
(45) Date of Patent: Feb. 14, 2023

(54) DATA PROCESSING APPARATUS AND METHOD

(71) Applicant: CANON MEDICAL SYSTEMS CORPORATION, Otawara (JP)

(72) Inventors: Owen Anderson, Edinburgh (GB); Aneta Lisowska, Edinburgh (GB); Alison O'Neil, Edinburgh (GB)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 224 days.

(21) Appl. No.: 16/749,395

(22) Filed: Jan. 22, 2020

(65) Prior Publication Data
US 2021/0225508 A1    Jul. 22, 2021

(51) Int. Cl.
G06N 3/08    (2006.01)
G16H 50/20   (2018.01)
G16H 30/40   (2018.01)
G06N 3/04    (2006.01)

(52) U.S. Cl.
CPC ............ G06N 3/08 (2013.01); G06N 3/0454 (2013.01); G16H 30/40 (2018.01); G16H 50/20 (2018.01)

(58) Field of Classification Search
CPC ......... G16H 10/00–80/00; G06N 3/00–99/007
See application file for complete search history.

(56) References Cited

U.S. PATENT DOCUMENTS

2002/0143761 A1* 10/2002 Shimano .............. G06F 16/583
2014/0088989 A1    3/2014 Krishnapuram et al.
2014/0172773 A1*  6/2014 Schmidt ................... G06N 7/00
                                                  706/54
2015/0095043 A1*  4/2015 Cordero Marcos .... G16H 20/17
                                                   705/2
2015/0193693 A1*  7/2015 Vasseur ............... H04L 63/1425
                                                  706/12
2016/0132787 A1*  5/2016 Drevo ..................... G06N 20/10
                                                  706/12
2018/0158552 A1   6/2018 Liu et al.
2018/0182096 A1   6/2018 Grady et al.
2018/0299869 A1* 10/2018 Yu ....................... G05B 19/4099
(Continued)

FOREIGN PATENT DOCUMENTS

EP        3582150 A1 * 12/2019 ............. G06N 3/084
WO   WO-2020223434 A1 * 11/2020 ............. A61B 5/055

OTHER PUBLICATIONS

Gang Luo, "A review of automatic selection methods for machine learning algorithms and hyper-parameter," Netw Model Anal Health Inform Bioinforma (2016) 5:18 (Year: 2016).*

(Continued)

Primary Examiner — Jonathon A. Szumny
(74) Attorney, Agent, or Firm — Oblon, McClelland, Maier & Neustadt, L.L.P.

(57) ABSTRACT

A medical system comprises processing circuitry configured to: receive a first trained model, wherein the trained model has been trained using a first data set acquired in a first cohort; receive a second data set acquired in a second cohort; input data included in the second data set and data representative of the first trained model into a second trained model; and receive from the second trained model an affinity-relating value which represents an affinity between the data included in the second data set and the first trained model.

17 Claims, 12 Drawing Sheets

(56) References Cited

U.S. PATENT DOCUMENTS

| | | | |
|---|---|---|---|
| 2019/0042940 A1* | 2/2019 | Sakairi | G06N 3/0454 |
| 2019/0138895 A1* | 5/2019 | Jin | G06N 3/0481 |
| 2019/0209022 A1* | 7/2019 | Sobol | A61B 5/7435 |
| 2019/0304603 A1* | 10/2019 | Takata | G16H 50/20 |
| 2019/0325354 A1* | 10/2019 | Rajnayak | G06K 9/6282 |
| 2019/0354850 A1* | 11/2019 | Watson | G06N 3/08 |
| 2019/0378533 A1* | 12/2019 | Chao | G10L 13/00 |
| 2020/0160212 A1* | 5/2020 | Shin | G06N 3/088 |
| 2020/0257999 A1* | 8/2020 | Narita | G06N 3/0427 |
| 2020/0320379 A1* | 10/2020 | Watson | G06N 3/08 |
| 2020/0334456 A1* | 10/2020 | Sridharan | G06K 9/00483 |
| 2020/0342409 A1* | 10/2020 | Jang | G06Q 10/1053 |
| 2021/0073377 A1* | 3/2021 | Coull | G06N 3/08 |
| 2021/0085397 A1* | 3/2021 | Passerini | G06N 3/0454 |
| 2021/0093301 A1* | 4/2021 | Wang | G06K 9/00221 |
| 2021/0103991 A1* | 4/2021 | Kern | G06Q 40/08 |
| 2021/0125104 A1* | 4/2021 | Christiansen | G06N 3/0454 |
| 2021/0183054 A1* | 6/2021 | Guo | G06T 7/174 |

OTHER PUBLICATIONS

Sujit et al., "EasyChair Preprint Automated Image Quality Evaluation of Structural Brain Magnetic Resonance Images using Deep Convolutional Neural Networks," EasyChair Preprint, No. 650. (Year: 2019).*

Chopra, S., Hadsell, R. and LeCun, Y., Jun. 2005, Learning a similarity metric discriminatively, with application to face verification. In CVPR (1) (pp. 539-546).

Vinyals, O., Blundell, C., Lillicrap, T., Kavukcuoglu, K., and Wierstra, D., 2016. Matching networks for one shot learning. In Advances in neural information processing systems (pp. 3630-3638).

R Devon Hjelm, Alex Fedorov, Samuel Lavoie-Marchildon, Karan Grewal, Phil Bachman, Adam Trischler, Yoshua Bengio, Learning deep representations by mutual information estimation and maximization https://arxiv.org/abs/1808.06670. (2019).

van de Ven, G.M. and Tolias, A.S., 2019. Generative replay with feedback connections as a general strategy for continual learning.

Ben-David, S., Blitzer, J., Crammer, K. and Pereira, F., 2007. Analysis of representations for domain adaptation. In Advances in neural information processing systems (pp. 137-144).

Zeng, G., Yang, X., Li, J., Yu, L., Heng, P.A. and Zheng, G., 2017, September. 3D U-net with multi-level deep supervision: fully automatic segmentation of proximal femur in 3D MR images. In International Workshop on Machine Learning in Medical Imaging (pp. 274-282). Springer, Cham.

Çalli, E., Murphy, K., Sogancioglu, E. and van Ginneken, B., 2019. FRODO: Free rejection of out-of-distribution samples: application to chest x-ray analysis.

* cited by examiner $$d = \begin{bmatrix} x_1 \\ x_2 \\ x_3 \\ x_1 \\ x_2 \\ \dots \\ a^1_1 \\ \dots \\ a^2_1 \\ a^2_2 \end{bmatrix} \quad m = \begin{bmatrix} w^1_{11} \\ w^1_{12} \\ w^1_{13} \\ w^1_{21} \\ w^1_{22} \\ \dots \\ w^2_{11} \\ \dots \\ 1 \\ 1 \end{bmatrix}$$

DATA PROCESSING APPARATUS AND METHOD

FIELD

Embodiments described herein relate generally to a method and apparatus for processing data, for example for determining an affinity between a data set and a trained model.

BACKGROUND

It is known to train machine learning algorithms to process data, for example medical data.

It is anticipated that in the future, machine learning algorithms will be trained at point-of-care, for example in a hospital. Training machine learning algorithms at the point of care may allow the fine-tuning of pre-existing models to perform on patient specific tasks. Allowing deep learning algorithm development to be conducted on-site with the data may circumvent barriers to data being taken off-site. For example, barriers to data being taken off-site may include data transfer agreements and other surrounding legal issues associated with sensitive data.

To facilitate the training of machine learning algorithms at point-of-care, it is anticipated that the process of developing a deep learning algorithm may be simplified. The process of developing a deep learning algorithm may then be considered to be de-skilled. Many steps and decisions that are currently made manually by data scientists may be automated in future.

In some circumstances, there may be an abundance of pre-trained models to choose from when approaching any new candidate task. The abundance of pre-trained model may be referred to as a model zoo. Some models may be better suited to a particular new task and/or set of new data than others. Some models may required less data to be fine-tuned.

Models may have limited support. Models may perform best in a domain in which they were trained. Models may perform best on data that is the same or similar to the data on which they were trained.

When applying machine learning (for example, when applying medical learning to medical tasks), fitting to a distribution of available data is performed. When using a model on target data, it may be desirable to measure how close the target data is to the source distribution of data on which the model was trained. The distribution on which the model is trained may be a distribution on which it is known that the model has adequate and well-tested performance. If the distance between the distribution on which the model was trained and a new distribution to which the model is to be applied is large, the model may be less applicable to the new distribution.

In some circumstances, it may be difficult to measure a difference between data sets. There are many axes along which a distance between data could be measured. For example, in the case of medical images, one could say that two images having identical mean and standard deviation of pixel intensities were coming from the same distribution. However, this method of assessment may not take into account that the medical images may have difference anatomical content, noise characteristics, alignment properties or other properties.

If data cannot be shared across institutions, there may not be information available about the data on which a given model is trained. Frequently, it may be difficult to obtain access to source data on which a model is trained, for example due to restrictive data sharing policies between institutions.

FIG. 1 is a schematic illustration of a process of model selection. A new data set 10 is obtained. The new data set may comprise, for example, imaging data, text data, structured data or a combination of heterogeneous data.

A plurality of trained models 12 is available. There is a question of which of the trained models 12 to use in processing the new data set 10. There may be differences in the data on which the trained models were trained. Each of the trained models 12 may have been trained on different data, for example data that differs in anatomy, modality, scanner, or population.

It may be desirable to process the data set 10 using the model which was trained on a data distribution most similar to that of the new data set 10, or using a plurality of models that were trained on a data distribution or distributions that were most similar to that of the new data set 10.

A data distribution 14 of the new data set 10 is represented in FIG. 1. FIG. 1 also shows data distributions 16A, 16B, 16C, 16D, 16E, 16F of some of the trained models 12. Data distribution 16A is most similar to the data distribution 14 of the new data set 10. Therefore, it may be desirable to process the new data set 10 using a trained model 12 that was trained on data distribution 16A.

However, as explained above, the data distribution on which the trained model 12 was trained may not be available. Access may be provided only to the trained models and not to the original training data.

In some circumstances, a generative model may be part of a trained model, for example as used in some modern continual learning set ups. See, for example, van de Ven, G. M. and Tolias, A. S., 2018, Generative replay with feedback connections as a general strategy for continual learning. If a generative model is part of the trained model, then a few samples can be generated. A generated data distribution may be compared to a data distribution 14 of the new data 10. For example, data distributions may be compared using A-distances. See, for example, Ben-David, S., Blitzer, J., Crammer, K. and Pereira, F., 2007. Analysis of representations for domain adaptation. In Advances in neural information processing systems (pp. 137-144).

In other circumstances, a model may be such that samples cannot be generated. It may not be possible to compare a new data distribution to a distribution of generated samples. It may not be possible to compare the new data distribution to the actual data on which the model was trained, if no access to the training data is provided.

BRIEF DESCRIPTION OF THE DRAWINGS

Embodiments are now described, by way of non-limiting example, and are illustrated in the following figures, in which.

DETAILED DESCRIPTION

Certain embodiments provide a medical system comprising processing circuitry configured to: receive a first trained model, wherein the trained model has been trained using a first data set acquired in a first cohort; receive a second data set acquired in a second cohort; input data included in the second data set and data representative of the first trained model into a second trained model; and receive from the second trained model an affinity-relating value which represents an affinity between the data included in the second data set and the first trained model.

Certain embodiments provide a method comprising: receiving a first trained model, wherein the trained model has been trained using a first data set acquired in a first cohort; receiving a second data set acquired in a second cohort; inputting data included in the second data set and data representative of the first trained model into a second trained model; and receiving from the second trained model an affinity-relating value which represents an affinity between the data included in the second data set and the first trained model.

Certain embodiments provide a medical system comprising processing circuitry configured to train a second model to output affinity-relating values which represent affinity between data samples of a data set and at least one first trained model, the training comprising: receiving training data comprising a plurality of data samples; receiving data representative of at least one first trained model; applying the at least one first trained model to the training data to obtain activation values; and using the training data, the data representative of at least one first trained model and the activation values for train the second model to output affinity-relating values.

Certain embodiments provide a method for training a second model to output affinity-relating values which represent affinity between data samples of a data set and at least one first trained model, the training comprising: receiving training data comprising a plurality of data samples; receiving data representative of at least one first trained model; applying the at least one first trained model to the training data to obtain activation values; and using the training data, the data representative of at least one first trained model and the activation values for train the second model to output affinity-relating values.

Figure 1:
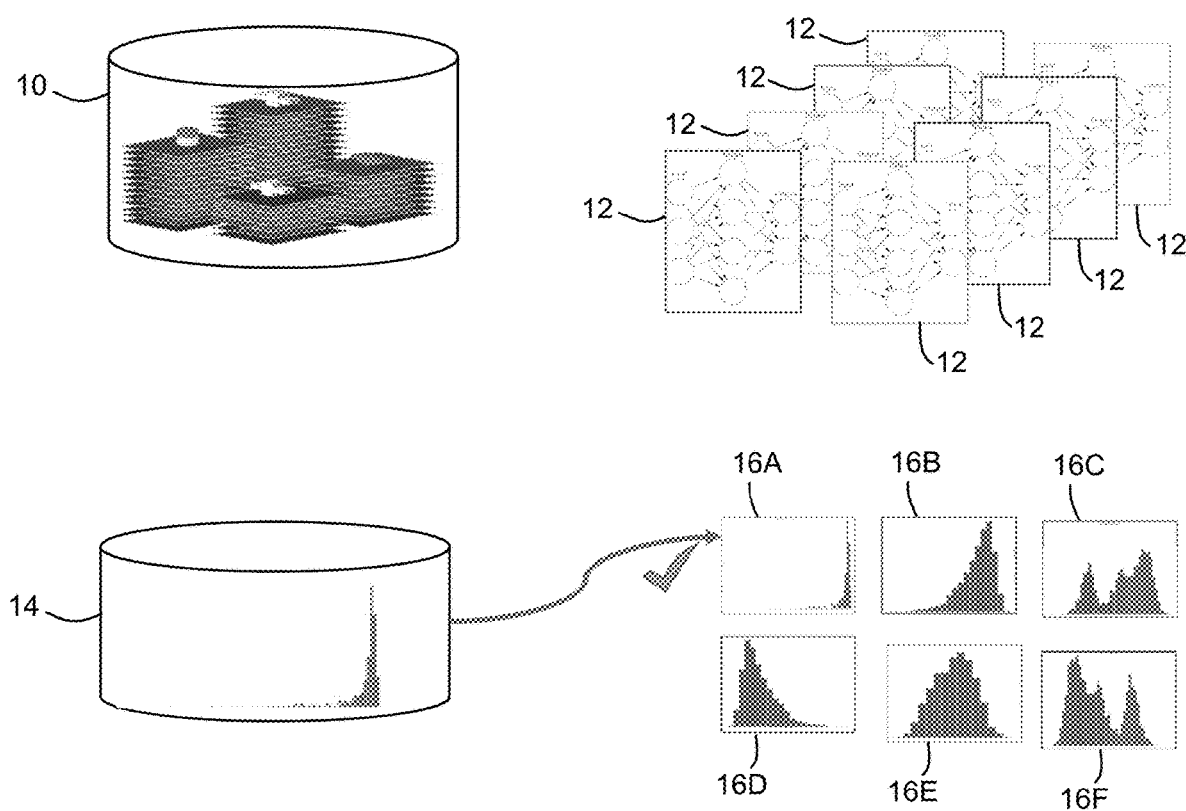
FIG. 1 is a schematic illustration of a process of model selection.
Figure 2:
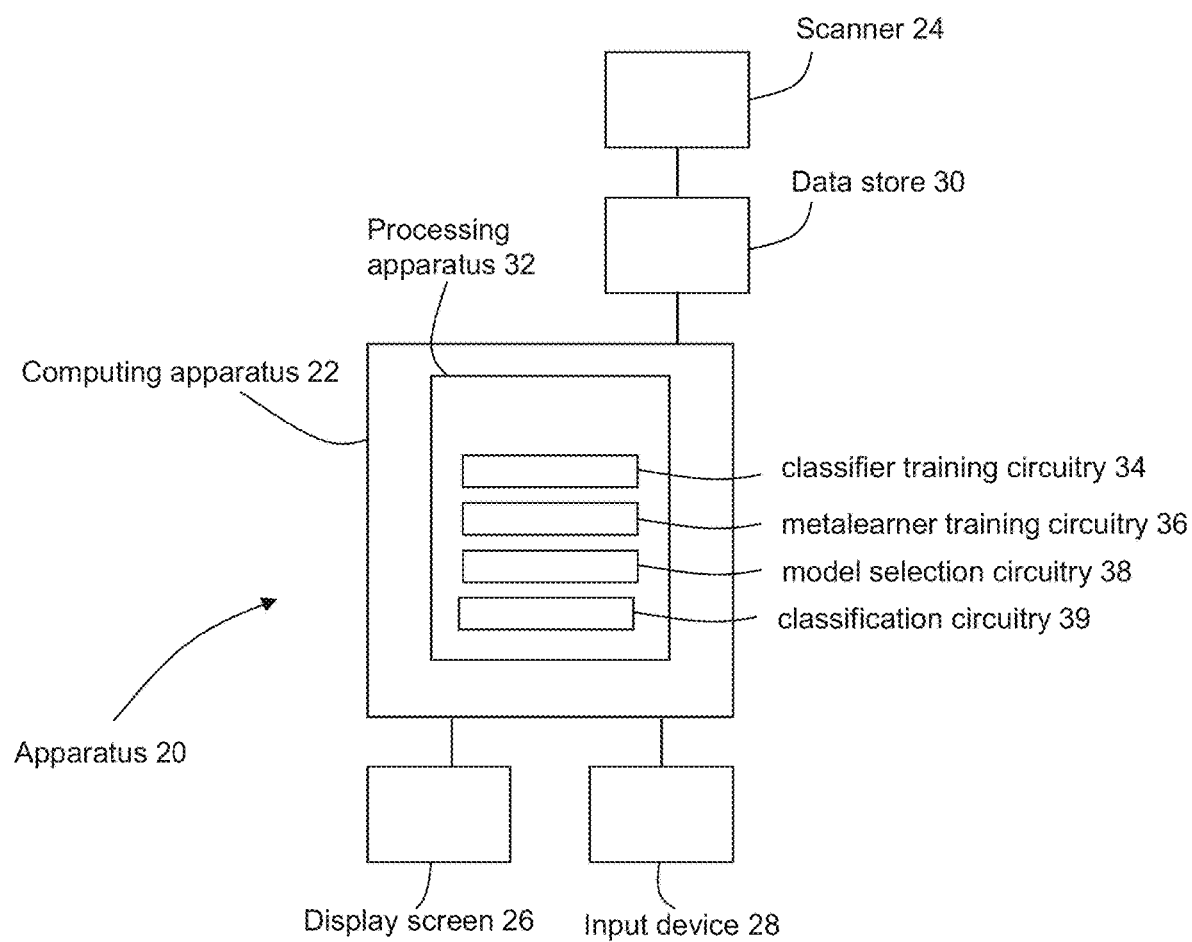
FIG. 2 is a schematic illustration of an apparatus in accordance with an embodiment.

A data processing apparatus 20 according to an embodiment is illustrated schematically in FIG. 2. In the present embodiment, the data processing apparatus 20 is configured to process medical image data. In other embodiments, the data processing apparatus 20 may be configured to process any appropriate data, for example imaging data, text data, structured data or a combination of heterogeneous data.

The data processing apparatus 20 comprises a computing apparatus 22, which in this case is a personal computer (PC) or workstation. The computing apparatus 22 is connected to a display screen 26 or other display device, and an input device or devices 28, such as a computer keyboard and mouse.

The computing apparatus 22 is configured to obtain image data sets from a data store 30. The image data sets have been generated by processing data acquired by a scanner 24 and stored in the data store 30.

The scanner 24 is configured to generate medical imaging data, which may comprise two-, three- or four-dimensional data in any imaging modality. For example, the scanner 24 may comprise a magnetic resonance (MR or MRI) scanner, CT (computed tomography) scanner, cone-beam CT scanner, X-ray scanner, ultrasound scanner, PET (positron emission tomography) scanner or SPECT (single photon emission computed tomography) scanner.

The computing apparatus 22 may receive medical image data from one or more further data stores (not shown) instead of or in addition to data store 30. For example, the computing apparatus 22 may receive medical image data from one or more remote data stores (not shown) which may form part of a Picture Archiving and Communication System (PACS) or other information system.

Computing apparatus 22 provides a processing resource for automatically or semi-automatically processing medical image data. Computing apparatus 22 comprises a processing apparatus 32. The processing apparatus 32 comprises classifier training circuitry 34 configured to train a first model to perform a classification task; metalearner training circuitry 36 configured to train a second model to determine matches and mismatches between a new data sample and a given source distribution; model selection circuitry 38 configured to use a metalearner to select at least one trained model; and classification circuitry 39 configured to classify data using the selected at least one trained model.

In the present embodiment, the circuitries 34, 36, 38, 39 are each implemented in computing apparatus 22 by means of a computer program having computer-readable instructions that are executable to perform the method of the embodiment. However, in other embodiments, the various circuitries may be implemented as one or more ASICs (application specific integrated circuits) or FPGAs (field programmable gate arrays).

The computing apparatus 22 also includes a hard drive and other components of a PC including RAM, ROM, a data bus, an operating system including various device drivers, and hardware devices including a graphics card. Such components are not shown in FIG. 2 for clarity.

Figure 3:
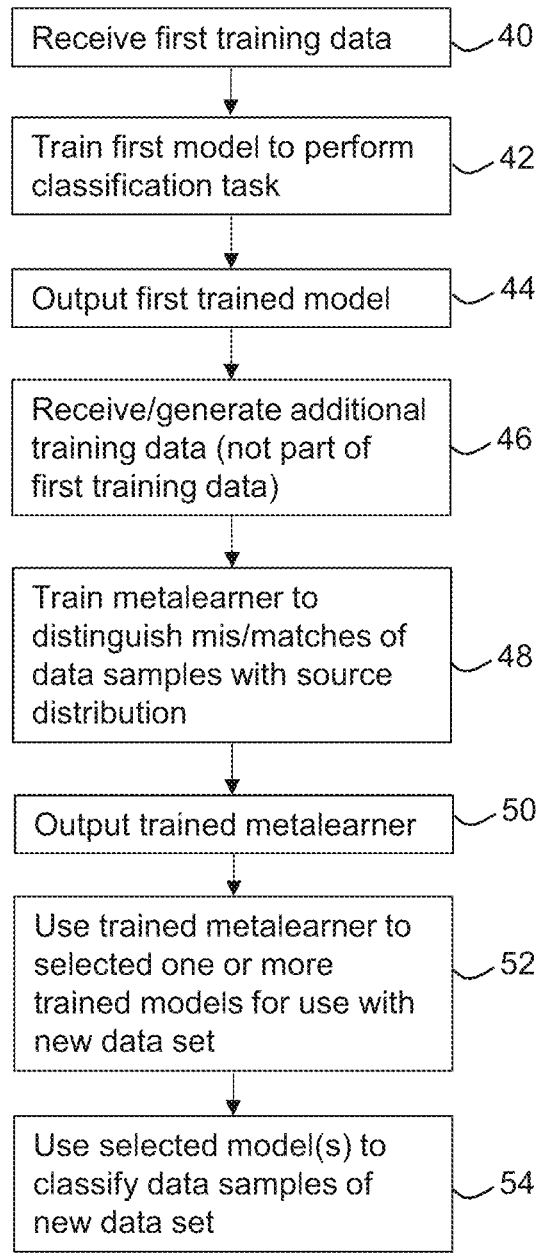
FIG. 3 illustrates in overview a model training method in accordance with an embodiment.

The data processing apparatus 20 of FIG. 2 is configured to perform the method of FIG. 3. The data processing apparatus 20 is configured to train a first model (which in the present embodiment is a classifier), to train a second model which may be referred to as a metalearner, and to use the metalearner to select one or more models to apply to new data based on respective affinity between each of the models and the new data. In other embodiments, different apparatuses may be used to perform the training of the first model and/or the training of the metalearner and/or the selection of one or more models to apply to new data.

Using the method of FIG. 3, a measure of an affinity between a model and new data may be obtained without access to the data on which the model has been trained. The measure of affinity may include a probability that the new data is from the same institution as the training data on which the model was trained. It may be possible to select models from a group of models that have been trained at different institutions, even if only the models and not their training data are available during the model selection.

At stage 40 of FIG. 3, the classifier training circuitry 34 receives from the data store 30 a first training data set for training a first model. The first training data set comprises data acquired in a first cohort. In the present embodiment, the first cohort comprises data acquired at a first institution, for example a first hospital. In other embodiments, the first cohort may comprise data acquired at and/or stored by any first entity. In some circumstances, data acquired at the first entity may not be available outside that entity. The data processing apparatus 20 may be situated within the first entity.

In the present embodiment, the first data set comprises image data acquired using the scanner 24. The first training data set comprises a plurality of data samples, each of the data samples comprising a respective medical image. In other embodiments, each of the data samples may comprise any suitable data type.

In the embodiment of FIG. 3, the first model is a neural network that is to be trained to perform a binary classification task. In other embodiments, the first model may comprise any suitable machine learning model and the classifier training circuitry 34 may be replaced or supplemented by any suitable training circuitry. The first model may be trained to perform any suitable data processing task, for example any suitable classification or regression. The first model may be trained to perform a segmentation. The first model may be trained to identify an anatomical feature or pathology.

At stage 42, the classifier training circuitry 34 uses the first training data set to train the first model to perform the binary classification task. The first model may be trained using any suitable model training method. In the present embodiment, the model training method comprises a supervised learning process. The first model is trained by minimizing a difference between binary classification values that are output by the model and ground truth classifications. In other embodiments, any suitable supervised or unsupervised learning process may be used to train the first model.

At stage 44, the classifier training circuitry outputs the trained first model.

Figure 4:
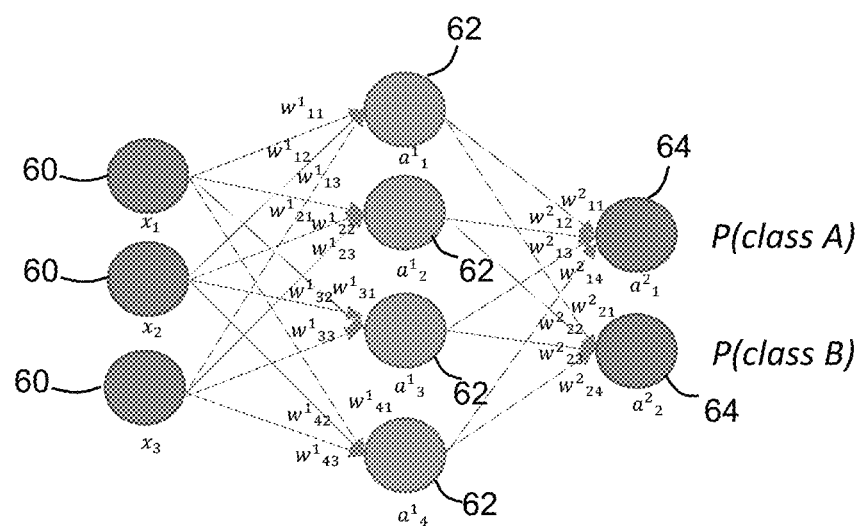
FIG. 4 is a simplified illustration of a trained model.

FIG. 4 shows a simplified illustration of the trained first model. The trained first model takes as its input 60 a set of data elements x from a data sample, for example a set of pixel intensity values. Only three data elements $x_1$, $x_2$, $x_3$ are shown in FIG. 4. In practice, there may be hundreds or thousands of data elements in a given data sample.

The first trained model comprises a first set of model weights $w^1$ which are applied to the data elements to obtain a set of activation values $a^1$ for a set of nodes 62 of the model. The first model further comprises a second set of model weights $w^2$ which are applied to the set of activation values a for the nodes 60 to obtain the model outputs 64. The outputs 64 have associated activation values $a^2$.

In the embodiment shown in FIG. 4, there are two model outputs 64. One is the probability P(class A) of a subject of the data sample being in class A. The other is the probability P(class B) of the subject of the data sample being in class B. In other embodiments, there may be any suitable number of model outputs 64.

During training, the weights $w^1$, $w^2$ of the first model are adjusted to improve the model's performance. Once the model has been trained, the model weights are fixed.

For simplicity, only a single layer comprising a single set of nodes 62 is illustrated in FIG. 4. In practice, the first model may comprise a plurality of layers, each having associated activation values a.

At stage 44, the classifier training circuitry 34 outputs the trained first model. The trained first model may be represented by the set of model weights $w^1$, $w^2$. The trained first model may be used to perform a binary classification by inputting a new data sample to the model inputs 60.

The metalearner training circuitry 36 receives the trained first model from the classifier training circuitry 34.

At stage 46, the metalearner training circuitry 36 receives from the data store 30 and/or from a further data store (not shown) a second training data set comprising a plurality of data samples. The second training data set comprises at least some of the data samples of the first training data set. The second training data set also comprises further data samples that do not form part of the first training data set. The further data samples may comprise simulated data or augmented data. The further data samples may comprise data samples that are deliberately selected to be bad matches with the first training data set on which the first trained model was trained.

At stage 48, the metalearner training circuitry 36 trains a second model 70, which may be referred to as a metalearner 70. In the description below, reference is made to training the metalearner 70 on the first trained model, which is trained to perform a binary classification. In other embodiments, the metalearner 70 may be trained on a plurality of trained models. The metalearner 70 may be trained on a plurality of similar models (for example, binary classifiers) that have been trained using different training conditions, for example using different random weight initializations. The metalearner 70 may be trained on a plurality of models that have been trained on different data sets and/or with different noise in a source distribution. The metalearner 70 may be trained on a combination of models which have be trained to perform any appropriate task or tasks. In some circumstances, model representations may be processed such that like-for-like nodes or filters are matched.

Any suitable method may be used to train the metalearner 70. For example, the metalearner 70 may be trained using a method that has been developed to train one-shot learning algorithms for similarity metric learning. See, for example, Chopra, S., Hadsell, R. and LeCun, Y., 2005, June. Learning a similarity metric discriminatively, with application to face verification. In CVPR (1) (pp. 539-546); Vinyals, O., Blundell, C., Lillicrap, T. and Werstra, D., 2016. Matching networks for one shot learning. In Advances in neural information processing systems (pp. 3630-3638).

Figures 5, 6:
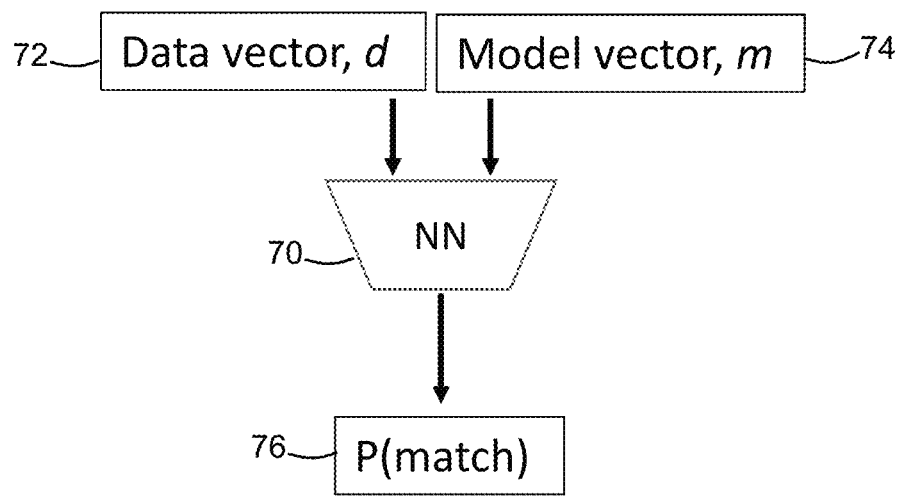
FIG. 5 shows examples of vectors d and m.
FIG. 6 is a schematic illustration of inputs and outputs of a metalearner in accordance with an embodiment.

In the present embodiment, the metalearner training circuitry 36 trains the metalearner 70 using a set of vector pairs (d, m). FIG. 5 shows an example of vectors d and m. In other embodiments, any suitable representation of the data may be used. Any suitable representation of the model may be used.

Vector m represents a trained model using a set of model weights. For example, the first trained model may be represented in a vector m comprising the weights $w^1$, $w^2$ of the first trained model. Vector m may be referred to as a model vector.

Vector d represents a data sample and the activation of a trained model by said data sample. Vector d comprises data elements x of the data sample plus a set of data activations a that occur in the trained model when the data sample is input to the first trained model. For example, for a data sample that has been input to the first trained model, the vector d comprises the data elements x of the data sample plus the activation values $a^1$, $a^2$ that result from applying the first trained model to the data sample. Vector d may be referred to as a data vector.

The metalearner training circuitry 36 trains the metalearner to determine whether each of the data samples was acquired in the first cohort or was not acquired in the first cohort. In the present embodiment, the first cohort comprises data acquired at a first institution. The data acquired at the first cohort has a distribution that may be referred to as a source distribution. A determination that the data sample was acquired at the first institution may be described as a match. A determination that the data sample was not acquired at the first institution may be described as a mismatch.

The metalearner learns to match the activation patterns produced by the input d with the model m. In the present embodiment, the metalearner 70 is trained in a supervised way by being provided with lots of data-model pairs, including both data samples that match with the source distribution and data samples that do not match with the source distribution.

FIG. 6 is a schematic illustration of the inputs and outputs of the metalearner 70. The metalearner is trained to receive a first input 72 comprising a data vector d for a data sample to which a model has been applied and a second input 74 comprising a model vector m for the model. The data vector d and model vector m are as described above with reference to FIG. 5.

The metalearner 70 is trained to output 76 a probability P(match) of whether the data sample of the data vector d matches a distribution on which the model was trained. The value for the probability P(match) may be referred to as an affinity-relating value. The probability P(match) is representative of an affinity between the data sample and the model. The probability P(match) is representative of an affinity between the data sample and the data on which the model was trained.

The metalearner 70 is trained using a loss function of binary cross-entropy (CE) for a P(match) value that is produced by the metalearner versus the true answer. The true answer denotes whether the data sample comes from the same institution at which the model was trained (same institution=1, match) or whether the data sample comes from a different institution (different institution=0, mismatch). The cross-entropy may be written as CE(P(match), Label(match)) where Label denotes the true answer.

In other embodiments, any suitable training method may be used to train the metalearner 70. The training of the metalearner 70 may be supervised or unsupervised.

At stage 50, the metalearner training circuitry 36 outputs the trained metalearner 70. The model selection circuitry 38 receives the first trained model (which in this embodiment is a trained classifier) and the trained metalearner 70. The model selection circuitry 38 also receives further trained models, which in the present embodiment are also trained classifiers. Some or all of the further trained models may have been trained on different data processing apparatuses. Some or all of the trained models may have been trained using data that is not available to the data processing apparatus 20.

The first trained model and the further trained models may be considered to form a set of candidate models 84. At stage 52, the model selection circuitry 38 applies the metalearner 70 to the set of candidate models 84 to select one or more of the candidate models using a method as illustrated in overview in FIG. 7.

Figure 7:
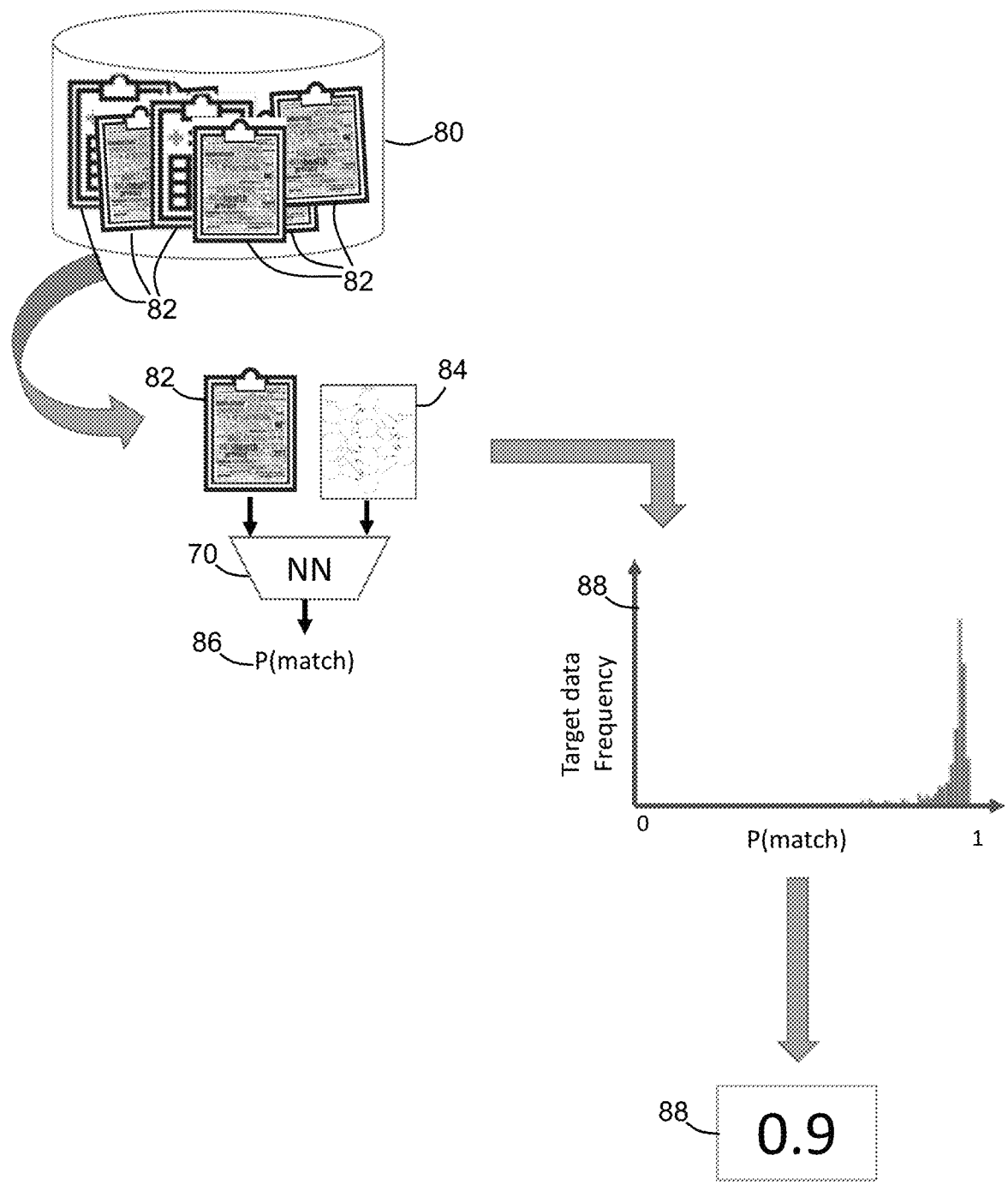
FIG. 7 illustrates in overview a method in accordance with an embodiment.

Turning to FIG. 7, the model selection circuitry 38 receives a target data set 80. The target data set 80 comprises a plurality of data samples 82. In the present embodiment, each data sample comprises a respective medical image.

FIG. 7 shows the process of applying the metalearner 70 to one of the candidate models 84 to determine a probability of match between the candidate model 84 and the target data set 80. The candidate model 84 may be described by vector m, which is representative of the weights of the candidate model.

For each candidate model 84, the model selection circuitry 38 applies the candidate model 84 to each of the data samples 82 in the data set 80. For each data sample 82, the model selection circuitry 84 obtains a data vector d which comprises data x of the data sample and a corresponding set of data activations a. The data activations a are representative of activations of the candidate model 84 when the data x is input to the candidate model 84.

For each of the data samples 82 in the target data set 80, the model selection circuitry 38 applies the metalearner 70 to the data vector d for the data sample 82 and the model vector m for the candidate model 84. d and m are input to the metalearner 70. The metalearner 70 outputs a value 86 for a probability of a match, P(match), for the data sample 82.

The model selection circuitry 38 aggregates the P(match) values for all of the data samples 82 in the target data set 80. FIG. 7 shows a plot 88 of the P(match) values. The plot 88 is a histogram plotting target data frequency against P(match) value. The plot 88 therefore shows how many times each P(match) value has occurred in the target data set 80.

If the candidate model 84 and the target data set 80 have a good match, it is expected that the plot 88 will show a distribution of matching probabilities that is skewed towards 1. Such a distribution is illustrated in FIG. 7.

In the present embodiment, the model selection circuitry 38 also obtains a single aggregated P(match) value 90 for the target data set 80. To obtain the single value 90 for the target data set, a metric such as the median may be used. In the example shown in FIG. 7, the value 90 for the median is 0.9. In other embodiments, any suitable method may be used to aggregate the P(match) values for the target data set 80. A value for any suitable metric may be obtained.

The model selection circuitry 38 compares the P(match) distribution and/or aggregated P(match) value for each candidate model 84 to the P(match) distribution and/or aggregated P(match) value for the other candidate models 84.

The model selection circuitry 38 selects one or more of the candidate models to use in classifying the new data set. The selection of the one or more of the candidate models 84 is based on the comparison of the P(match) distribution and/or aggregated P(match) value for each of the candidate models 84. For example, the model selection circuitry 38 may select the candidate model 84 having the highest aggregated P(match) value. The model selection circuitry 84 may select a number (for example, 2, 3, 4 or 5) of candidate models 84 having the highest aggregated P(match) value. In other embodiments, the model selection circuitry 84 may select all candidate models having an aggregated P(match) value that is above a threshold value.

The model selection circuitry 38 outputs a selection of one or more candidate models 84. The classification circuitry 39 receives the selected one or more candidate models 84.

We return to the flow chart of FIG. 3. The output of stage 50 is the one or more selected models 84.

At stage 54, the classification circuitry 39 uses the selected one or more candidate models 84 to classify data samples of the target data set 80. In the present embodiment, the selected models 84 each perform a binary classification. In other embodiments, the selected models 84 may be models that are trained to perform any suitable task, for example any suitable classification, regression, segmentation or identification.

In the method of FIG. 3, the metalearner 70 is used to determine which of a plurality of trained models 84 is the most appropriate for a trained data set 80. The metalearner 70 may be used to determine suitability of candidate models 84 even if the training data sets on which the candidate models 84 were trained are not accessible to the metalearner 70.

It is known that the candidate models may typically have limited support. Models may perform best in the domain they were trained, or on the source data. The method of FIG. 3 may be used to match models to data. The metalearner 70 may be used to quantify a distance between domains.

The metalearner 70 learns to map data (model activation) to a model (weights). The metalearner 70 may learn to distinguish between normal activations which may occur when a model is applied to data similar to that on which is trained, and abnormal activations which may occur when a model is applied to data that is less similar to that on which it is trained. In some circumstances, the metalearner 70 may generalize to models other than the model or models on which it is trained.

The metalearner 70 may match models to data distributions even when the data distributions are complex. For example, the data distributions may relate to intensities, anatomical content, noise characteristics and/or alignment properties.

The use of the metalearner 70 may facilitate selection of a model from a plurality of candidate models, for example from a model zoo. The metalearner 70 may select models automatically, with minimal expert input. The use of a metalearner 70 may make it more straightforward to use trained models at institutions other than the institution at which a given model was trained.

The metalearner 70 may be used to select models in a federated learning setup in which models are trained at multiple institutions. Data from each institution may not be available to other institutions.

The metalearner 70 may be used to select training data on which to train a model. The metalearner 70 may be used to select a trained model before fine-tuning that model with further training. In some circumstances, less specialist input may be needed to fine-tune a model if information about the model has been obtained by the metalearner 70. The metalearner 70 may be used to select a trained model to which knowledge is to be added by continual learning.

In some embodiment, a separate metalearner is trained for each task and model architecture. In other embodiments a metalearner may generalize between tasks and/or architectures.

In some embodiments, a metalearner is trained on a single model and is only used on the model on which it is trained. In other embodiments, a metalearner is trained on multiple models. The metalearner may be a general metalearner that can work for unseen models.

To train the metalearner, the metalearner may be provided with examples of annotated data for which each model does well, and examples of annotated data for which each model does poorly. In some circumstances, the metalearner does not have access to data on which one or more of the models was trained. In general, the metalearner may be provided with access to annotated examples (comprising data and labels) in both categories (good performance, bad performance) across the models. In some circumstances, the best performance of the metalearner may be obtained when examples of both categories are available for every model.

In some embodiments, the performance of a model is used as a proxy for training distribution. If the model performs well on given data, it may be assumed that the data is within a distribution similar to that on which the model was trained. If the model performs poorly on given data, it may be assumed that the data is out of distribution.

In the embodiment described above, the first model (which in the present embodiment is a binary classifier) and the metalearner 70 are each trained by the data processing apparatus 10. The data processing apparatus 10 applies the metalearner 70 to select models, which may include the first model.

In other embodiments, the first model and metalearner 70 are each trained by an apparatus different from the apparatus at which they are applied. In some circumstances, the first model is trained by one apparatus and the metalearner 70 is trained by a different apparatus.

In one embodiment, the data processing apparatus 10 at a first institution trains a first model and a metalearner 70 on data held at that institution. The data processing apparatus 10 provides the trained first model and the trained metalearner 70 to a second apparatus that is outside the first institution. For example, the second apparatus may be an external server. The external server may comprise a centralized repository. The external server may comprise a server at another entity, for example at a different hospital.

The training data set is not provided to the external server. Data restrictions may be such that the training data set is not permitted to leave the first institution. The first model and metalearner 70 were each trained on data from the first institution, but do not comprise data from the first institution. Therefore, it may be permissible to provide the trained first model and/or metalearner 70 to the external server.

The external server stores a plurality of trained models, including the first trained model. The plurality of models may be referred to as a model zoo. The plurality of models comprises multiple models that are trained to perform the same task. The models have been trained on different data cohorts. For example, the models may have been trained at different institutions.

The metalearner 70 may be used at the external server to select one or more of the trained models to be used on a target data set, as described above with reference to FIGS. 3 and 7.

In the embodiment described above with reference to FIGS. 3, 6 and 7, the metalearner 70 is trained to distinguish between data samples that come from the same institution on which a candidate model 84 was trained, and data samples that come from a different institution than the one on which the model was trained. A cross-entropy for the metalearner's output and the true answer is used.

In further embodiments, the metalearner's output is weighted by the accuracy of the candidate model 84 for the task that the candidate model 84 is trained to perform. In such a case, the cross-entropy with which the metalearner is trained may be written as:

Weighted_CE(P(match), Label(match), P(true class))

In some circumstances, matching only to the source distribution of each model 84 may not provide the best result. For example, if a data sample comes from institution A but a model 84 trained at institution A performs poorly for that sample (perhaps because institution A has little data), then a match between the institution A and the data sample may be considered to be invalid.

In some circumstances, a model trained on data from institution B may perform well for a data sample from institution A. For example, the populations of institution A and institution B may be similar. Institution B may have more data available than institution A. If a data sample comes from institution A but a model trained on data from institution B does well for that data sample, a mismatch between the data sample and institution B may be considered to be invalid.

A weighting factor may be added to the cross-entropy. The weighting factor may be added to account for the possibility of a model performing well on data from a different institution and/or a model performing poorly on data from its own institution. The weighting factor may be derived from the performance of the model on the data sample.

If the task is classification, the cross-entropy may be weighted by the accuracy of the model of the data sample, P(true class).

In the equation below, P(match) is written as $P_{Match}$, Label(match) is written as $Y_{Match}$, P(class) is written as $P_C$ and Label(class) is written as P(class) or $P_C$ is the output of the model, which provides a probability of a binary classification. Label(class) or $Y_C$ is the ground truth value for the classification.

$$CE(P_{Match}, Y_{Match}) = Y_{Match} \log(P_{Match}) + (1 - Y_{Match}) \log(1 - P_{Match})$$

$$\text{Weighted\_CE}(P_{Match}, Y_{match}, P_C, Y_C) = \Sigma_{c=1}^{n} Y^c [P^c Y^{Match} \log(P^{Match}) + (1 - P^c)(1 - Y^{Match}) \log(1 - P^{Match})]$$

The weighted cross-entropy may be used to train the metalearner 70.

By including performance of the model 84 when training the metalearner 70, model selection may be improved. The model selection circuitry 38 may use the metalearner 70 to select one or more models 84 for use of a target data set based not only on the similarity of the target data set to the data sets on which the models were trained, but also on the performance of the models 84. Models 84 that do not have good performance on given target data may be downweighted, even if the model 84 was trained using similar data to the target data.

In the embodiment shown in FIG. 4, only one layer of nodes 62 was shown in the first model. The metalearner 70 was trained on activation values $a^1$ from the nodes 62 and activation values $a^2$ from the outputs 64, where the activation values $a^2$ from the outputs 64 are the class probabilities themselves.

In many embodiments, the trained first model (for example, a classification or regression model) is a neural network comprising multiple layers. In some embodiments, a layerwise metalearner is used. The layerwise metalearner may learn from early activations as well as from later ones. For example, the metalearner may comprise multiple metalearners desired from successive intermediate levels. The use of an ensemble of multiple layers may be considered to be similar to the idea of deep supervision, for example as described in Zeng, G., Yang, X., Li, J., Yu, L., Heng, P. A. and Zheng, G., 2017, September. 3D U-net with multi-level deep supervision: fully automatic segmentation of proximal femur in 3D MR images. In *International Workshop on Machine Learning in Medical Imaging* (pp. 274-282). Springer, Cham.

Figure 8:
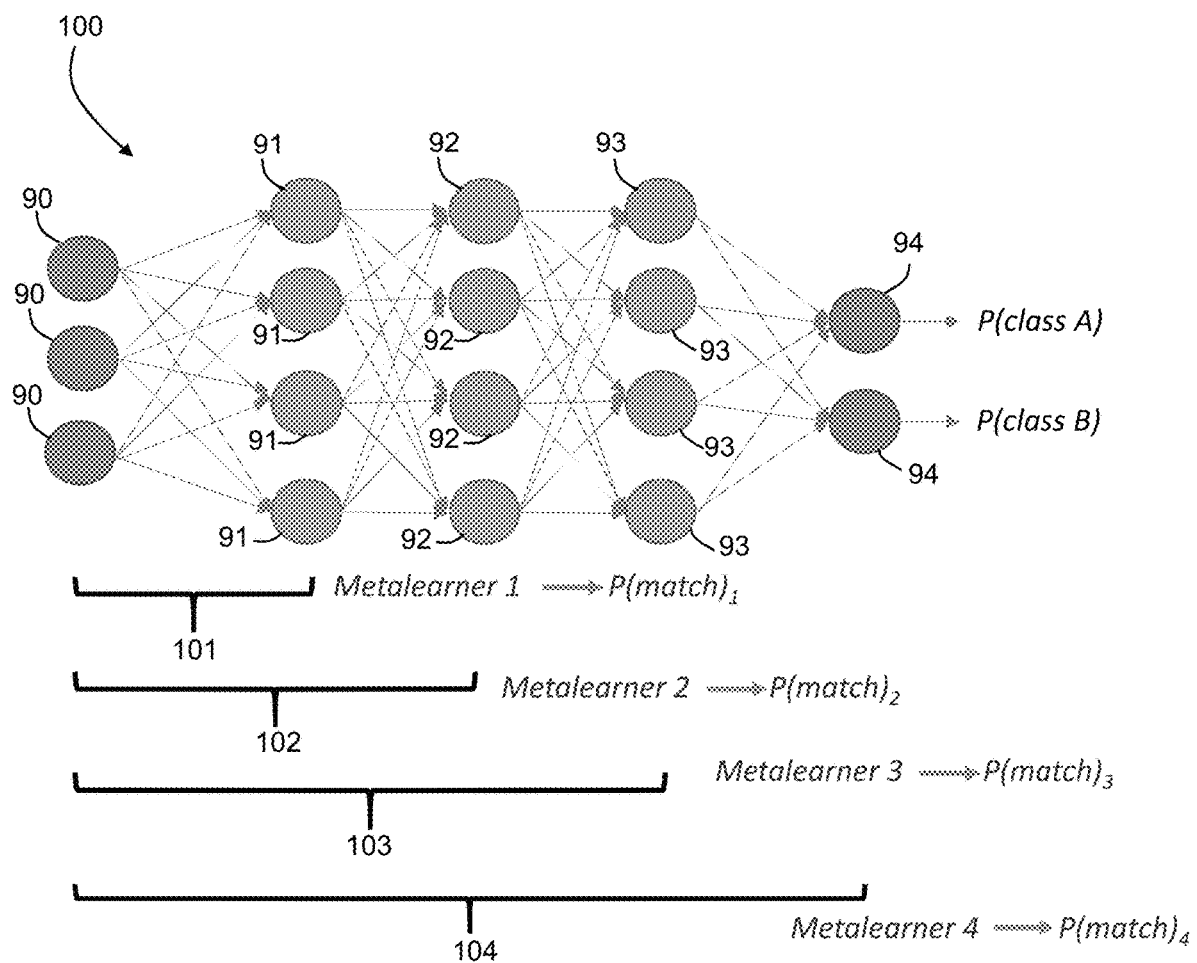
FIG. 8 is a schematic illustration of a layerwise metalearner in accordance with an embodiment.

FIG. 8 is a schematic illustration of an embodiment of a layerwise metalearner. A neural network 100 comprises inputs 90, three layers of nodes 91, 92, 93 and outputs 94. The outputs 94 comprise binary classification probabilities P(class A), P(class B).

A first metalearner 101 is trained using values for the inputs 90 and for activations of the first layer 91. The first metalearner 101 may be trained using any suitable method, for example using a method as described above with reference to FIGS. 3 and 7. It is noted that the first metalearner 101 does not use activations for layers 92, 93 or for the final outputs 94. The first metalearner 101 is trained to output a first probability of a match, $P(\text{match})_1$.

A second metalearner 102 is trained using values for the inputs 90 and for activations of the first layer 91 and second layer 92. The second metalearner 102 may be trained using any suitable method, for example using a method as described above with reference to FIGS. 3 and 7. The second metalearner 102 does not use activations for layer 93 or for the final outputs 94. The second metalearner 102 is trained to output a second probability of a match, $P(\text{match})_2$.

A third metalearner 103 is trained using values for the inputs 90 and for activations of the first layer 91, second layer 92 and third layer 93. The third metalearner 103 may be trained using any suitable method, for example using a method as described above with reference to FIGS. 3 and 7. The third metalearner 103 does not use activations for the final outputs 94. The third metalearner 102 is trained to output a third probability of a match, $P(\text{match})_3$.

A fourth metalearner 104 is trained using values for the inputs 90 and for activations of the first layer 91, second layer 92, third layer 93 and outputs 94. The fourth metalearner 104 may be trained using any suitable method, for example using a method as described above with reference to FIGS. 3 and 7. The fourth metalearner 104 is trained to output a fourth probability of a match, $P(\text{match})_4$.

Once trained, model selection circuitry 38 uses the ensemble of metalearners 101, 102, 103, 104 to determine a match between a candidate model 84 and a target data set 80. In the embodiment of FIG. 8, for each data sample in the target data set 80, the model selection circuitry 38 obtains a weighted sum of $P(\text{match})_1$, $P(\text{match})_2$, $P(\text{match})_3$, and $P(\text{match})_4$ for the data sample.

$$P(\text{match}) = \Sigma_{x=1}^{n} w_x P(\text{match})_x$$

The model selection circuitry 38 obtains the weighted sum of the estimated matching probabilities $P(\text{match})_1$, $P(\text{match})_2$, $P(\text{match})_3$, and $P(\text{match})_4$ using a set of weights $w_x$ with x from 1 to 4. In some embodiments, the weights $w_x$ may be learned during training of the ensemble of metalearners 101, 102, 103, 104.

By using multiple metalearners 101, 102, 103, 104, features at different levels of the neural network may be captured. Towards the input, it may be expected that generic features may be extracted, for example edges. Towards the output, more complex or specific features may be extracted. In some circumstances, a better identification of unusual activation patterns may be obtained when metalearners that act on different layers of the neural network are combined.

In some embodiments, layerwise convolutional kernels (applied to all nodes/kernels in a layer) and/or layerwise max pooling operations may be used.

For convolutional neural network models as applied to images, a metalearner may depend on learning characteristic spatial patterns in the activations across the voxelwise input. The spatial patterns in the activations may be referred to as characteristic feature maps. In some embodiments, the metalearner is provided with the intermediate feature maps.

Figure 9:
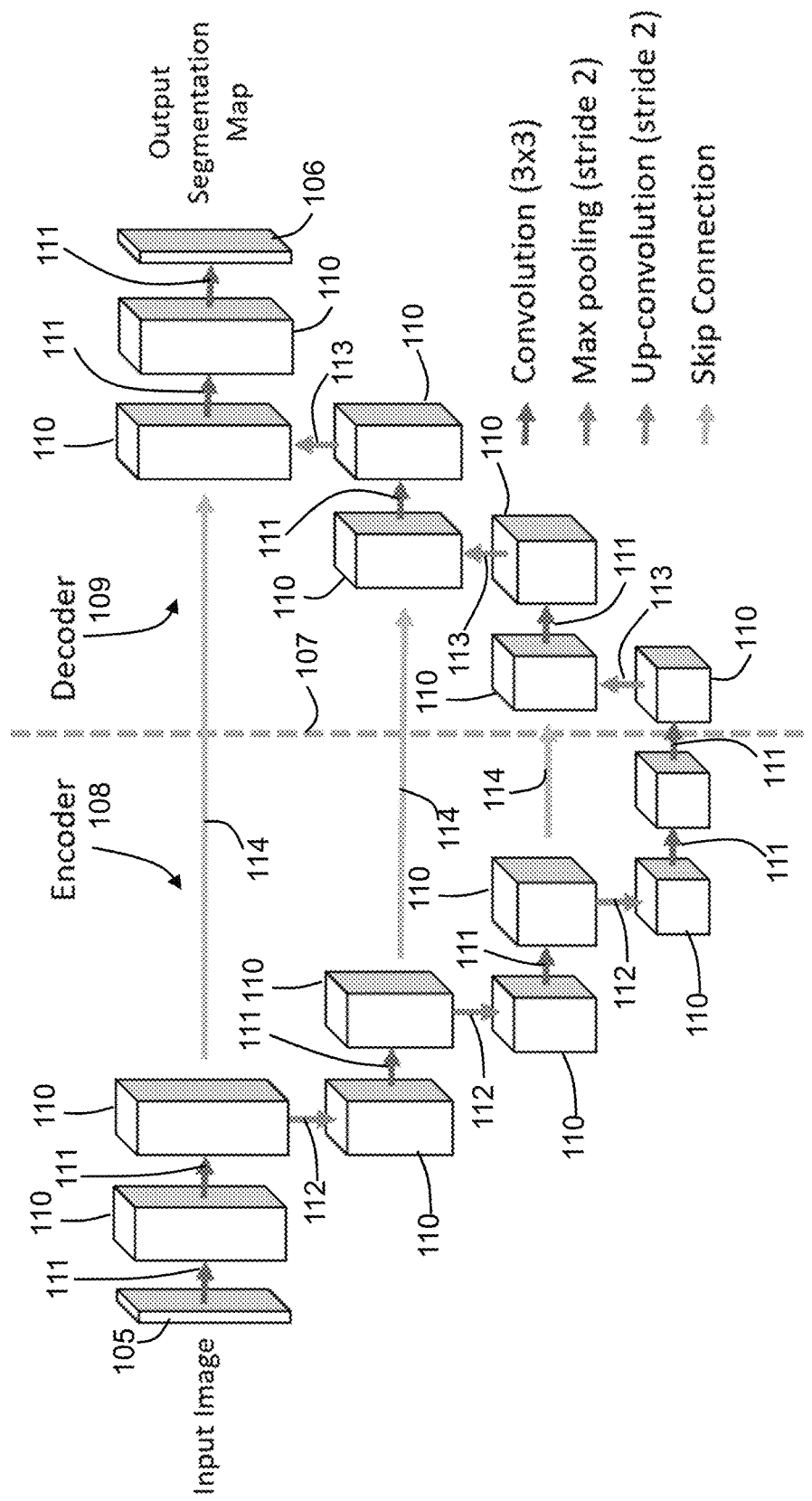
FIG. 9 is a schematic diagram of a trained model which comprises a U-Net.

FIG. 9 is a schematic diagram of a trained model which comprises a U-Net. An image file 105 is input to the U-Net. A encoder stage 108 of the U-Net reduces a resolution of the image. A decoder stage 109 results in a high-resolution output image 106, which in the present embodiment is a segmentation map. In the schematic diagram of FIG. 9, a dividing line 107 separates the part of the diagram representing the encoder stage 108 and the part of the diagram representing the decoder stage 109.

The model comprises a set of layers 110. Arrows 111 are representative of convolution operations, which in this example are 3×3 convolutions. Arrows 112 are representative of max pooling operations, which in this example have stride 2. Arrows 113 are representative of up-convolution operations, which in this example have stride 2. Arrows 114 are representative of skip connections.

All of the blocks shown in the U-Net diagram may be possible inputs to a metalearner for the segmentation task performed by the U-net. The metalearner may look at activations across the image and learn spatial information. In the case of image data, a prediction is known for each pixel and also for its neighbors. The metalearner may be presented with information for the whole image at once. The metalearner may be presented with some or all of the feature maps that are generated by the U-Net.

Figure 10:
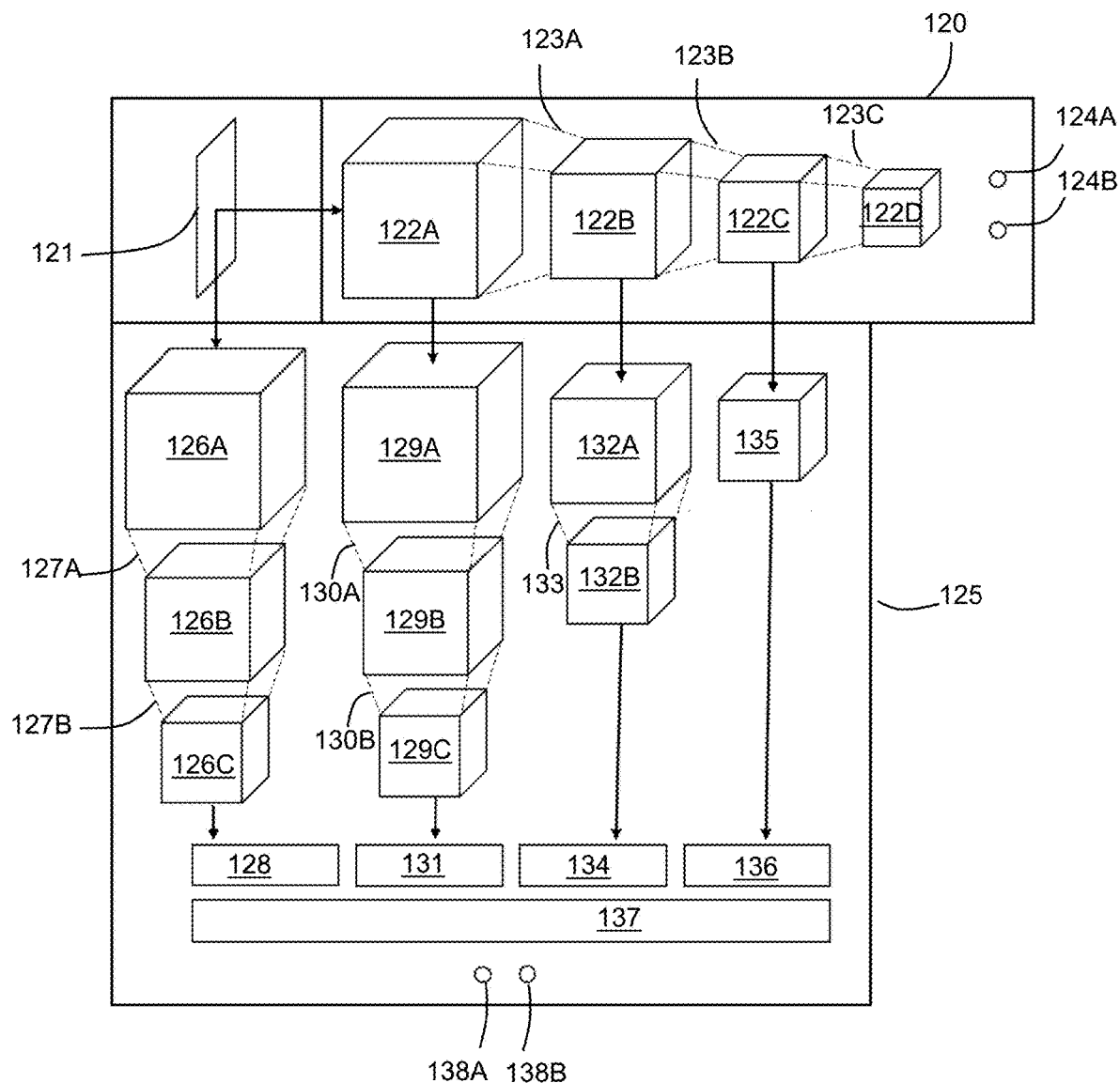
FIG. 10 is a schematic diagram illustrating in overview a classifier and metalearner that were trained as a prototype.

In some embodiments, the model weights are not input into the metalearner. Instead, the model receives spatial patterns between the activations. The use of spatial patterns of activations may be particularly appropriate to convolutions imaging models. FIG. 10 is a schematic diagram illustrating in overview a classifier 120 and metalearner 125 that were trained as a prototype.

A first model, classifier 120, was trained to classify 1s and 0s from the MNIST (Modified National Institute of Standards and Technology) database of handwritten digits. The classifier 120 receives an input image 121. The input image 121 passes through four layers 122A, 122B, 122C, 122D via pooling operations 123A, 123B, 123C to obtain an output which comprises a prediction 124A, 124B of whether the input image 121 represents a 1 or a 0. The intermediate activations at layers 122, 123, 124, 125 are feature maps.

A second model, metalearner 125 was trained on the intermediate feature maps from layers 122A, 122B, 122C, 122D of the classifier 120. The metalearner 125 received a data representation d. The metalearner did not receive the model weights.

In the metalearner 125 of FIG. 10, the input image 121 passes through convolution layers 126A, 126B, 126C via pooling operations 127A, 127B to obtain a densely connected layer 128. The feature map from layer 122A passes through convolution layers 129A, 129B, 129C via pooling operations 130A, 130B to obtain a densely connected layer 131. The feature map from layer 122B passes through convolution layers 132A, 132B via pooling layer 133 to obtain a densely connected layer 133. The feature map from layer 122C passes through convolution layer 132 to obtain a densely connected layer 136. Features of the densely connected layers 128, 131, 134, 136 are merged to obtain a further densely connected layer 137. The metalearner 125 outputs a prediction 138A, 138B of whether or not the data matches the distribution on which the model 120 was trained.

The metalearner 125 was trained using 0s and 1s as matched data, and 2s, 3s, 4s, 5s, 6s and 7s as the unmatched data. The metalearner 125 was trained to return a match when the activations of the classifier 120 correspond with an input that is a 0 or 1, and to return a mismatched when the activations of the classifier 120 correspond with an input that is a 2, 3, 4, 5, 6 or 7. Straight cross-entropy was used as the loss function.

The model was tested on a held back set of images. The held back set of images contained new images of the classes that the classifier 120 had been trained to distinguish (0s and 1s), and unseen data (0s, 1s, 2s, 3s, 4s, 5s, 6s, 7s, 8s and 9s).

In training, the metalearner 125 had learned that 0s and 1s match the classifier 120, and 2s to 7s are mismatched with the classifier 120.

Figure 11:
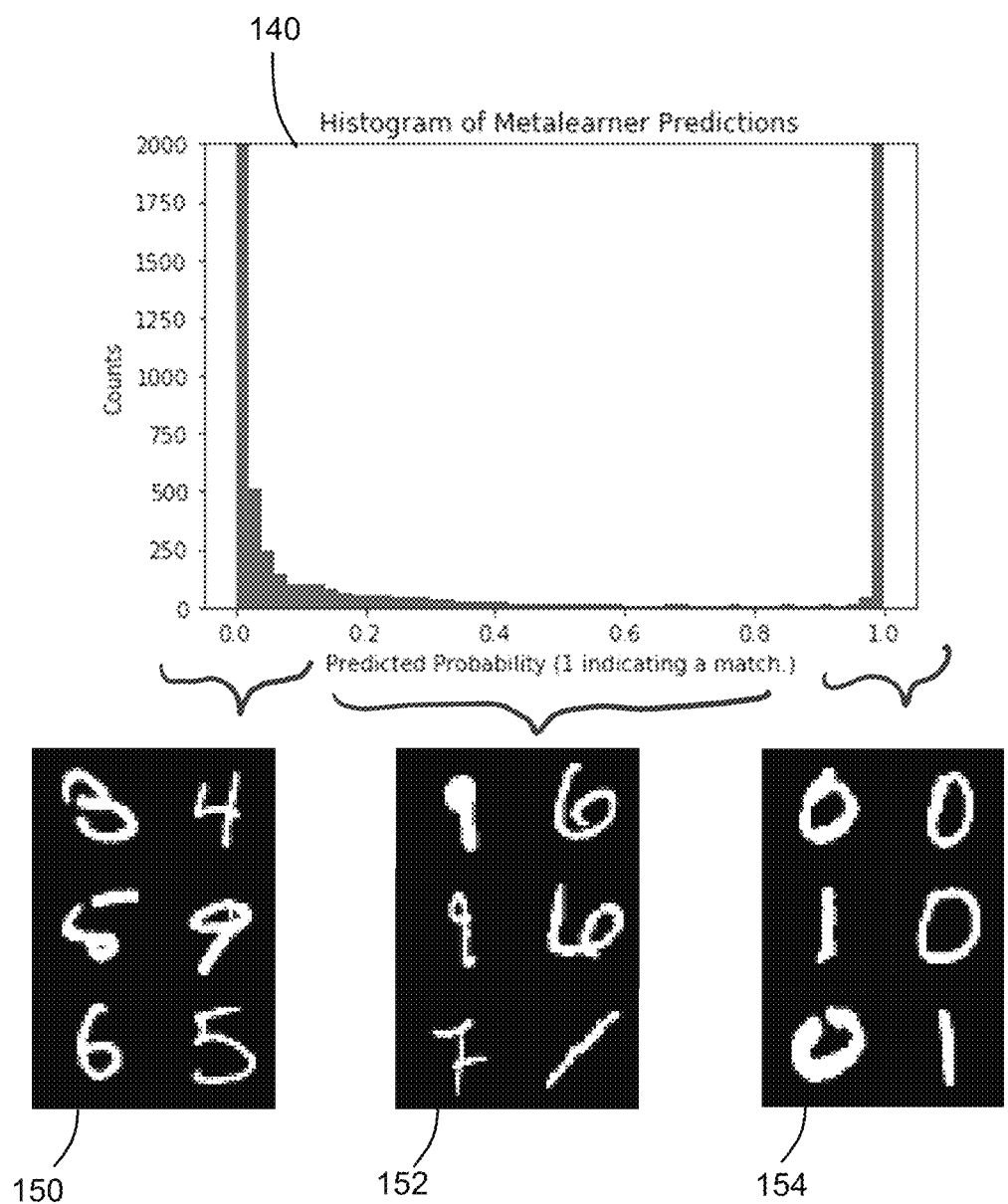
FIG. 11 is a histogram of probabilities predicted by a metalearner in accordance with a prototype.

FIG. 11 shows a histogram 140 of probabilities of match predicted by the metalearner 125 across the test set. The histogram plots counts versus predicted probability, where 1 indicates a match and 0 indicates a mismatch.

FIG. 11 also shows images 150, 152, 154 sampled from different areas of the graph. Images 150 are images for which the metalearner outputs a low probability. It was found that the metalearner 125 outputs a low probability for mismatches on which it was trained (2s, 3s, 4s, 5s, 6s and 7s). It was also found on this test set that the metalearner 125 was able to generalize to the unseen. The metalearner 125 was able to generalize to examples (8s and 9s) that the metalearner 125 had not been explicitly trained to identify as unusual.

Images 152 are images for which the metalearner 125 outputs a probability in the central region of the graph. The probability is neither very low or very high. It may be seen that images sampled from the center of the graph have many similar features to the matched distribution of 1s and 0s. For example, the images 152 include some 9s and 6s that are written in such a way to look similar to 1s and 0s. The images 152 also include a 1 which has been rotated.

Images 154 at the high probability end of the graph are 1s and 0s. The metalearner has correctly learned that 1s and 0s match the model.

Figure 12:
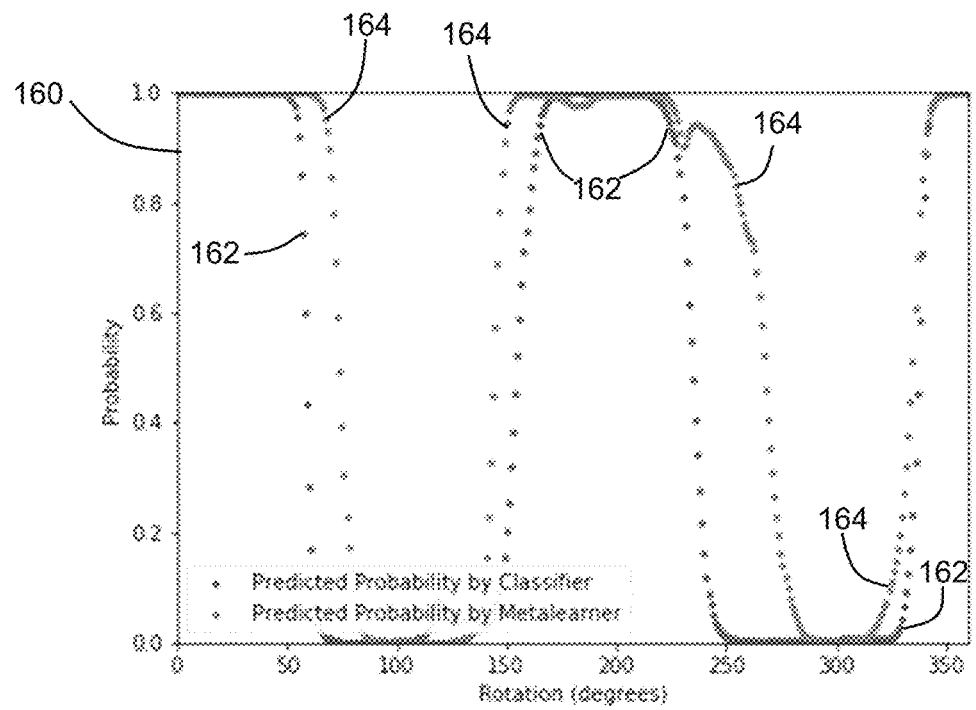
FIG. 12 is a plot of probabilities against rotation angle.

The metalearner 125 was also tested on a matched example (a number 1) as it was rotated through 360 degrees. The classifier 120 had been trained on numbers having a standard orientation. FIG. 12 plots the classifier's classification of the number 1 as it was rotated, and the metalearner's predictions based on the activations of the classifier 120 in response to the number 1 as it was rotated. Probabilities are plotted against rotation angle in degrees.

The prediction of the classifier 120 is shown by points 162. A prediction value of 1 indicates a prediction of number 1, and a prediction value of 0 indicates a prediction of number 0. It can be seen from points 162 that when the example number 1 is rotated by 90 degrees, the classifier 120 classifies the image incorrectly. When the number 1 is rotated by 90 degrees, the classifier classifies the image as a 0. This is because the input data at 90 degrees is outside the limited support of the training data.

The prediction of the metalearner 125 is shown by points 164. A value of 1 indicates that the metalearner 125 has determined a match with the model. A value of 0 indicates that the metalearner has determined a mismatch with the model 120. The metalearner 125 correctly identifies that the image at 90 degrees of rotation does not match the model 120.

Figure 13:
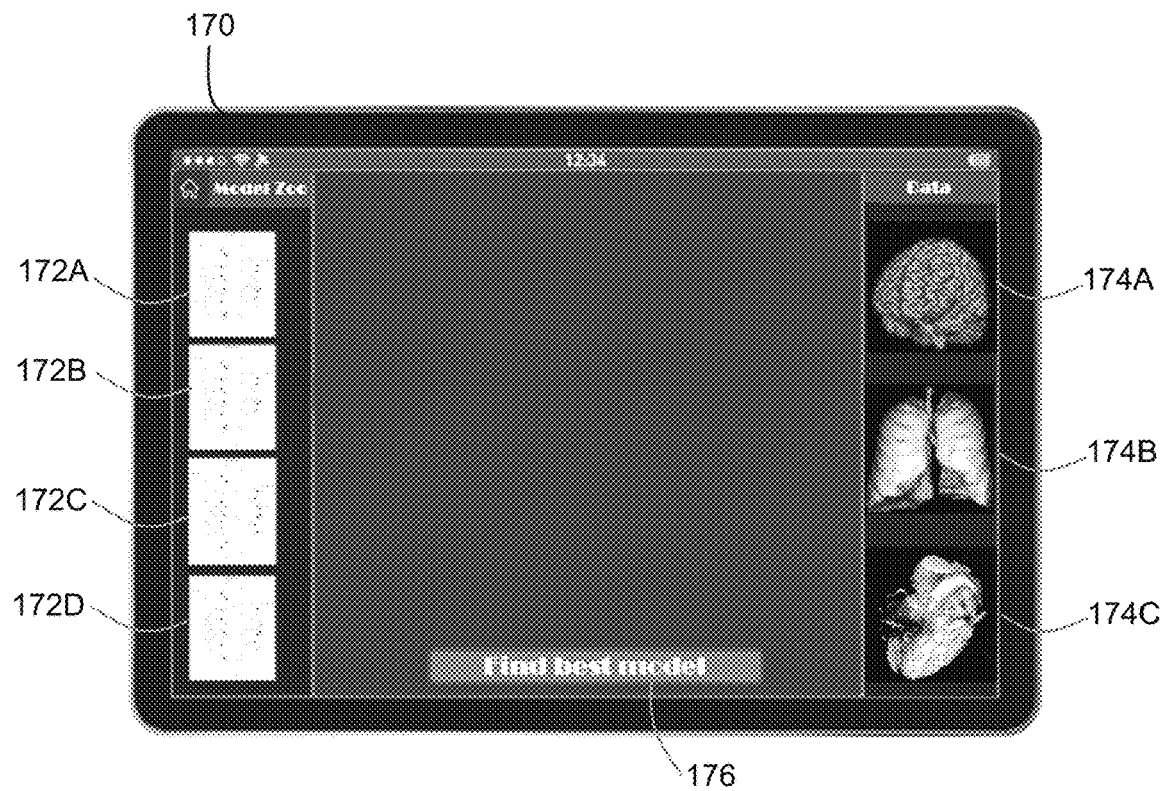
FIG. 13 is a schematic illustration of a user interface in accordance with an embodiment.
Figure 14:
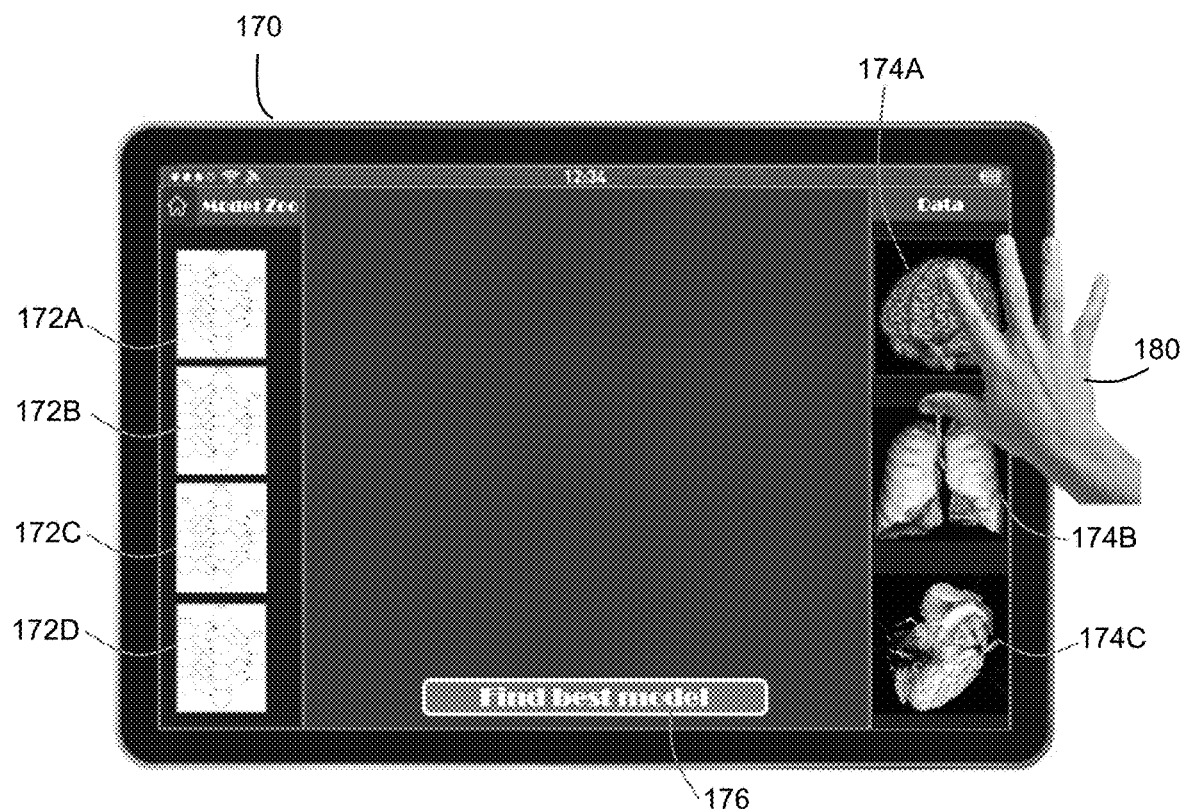
FIG. 14 is a schematic illustration of the use of the user interface of FIG. 13 by a user.
Figure 15:
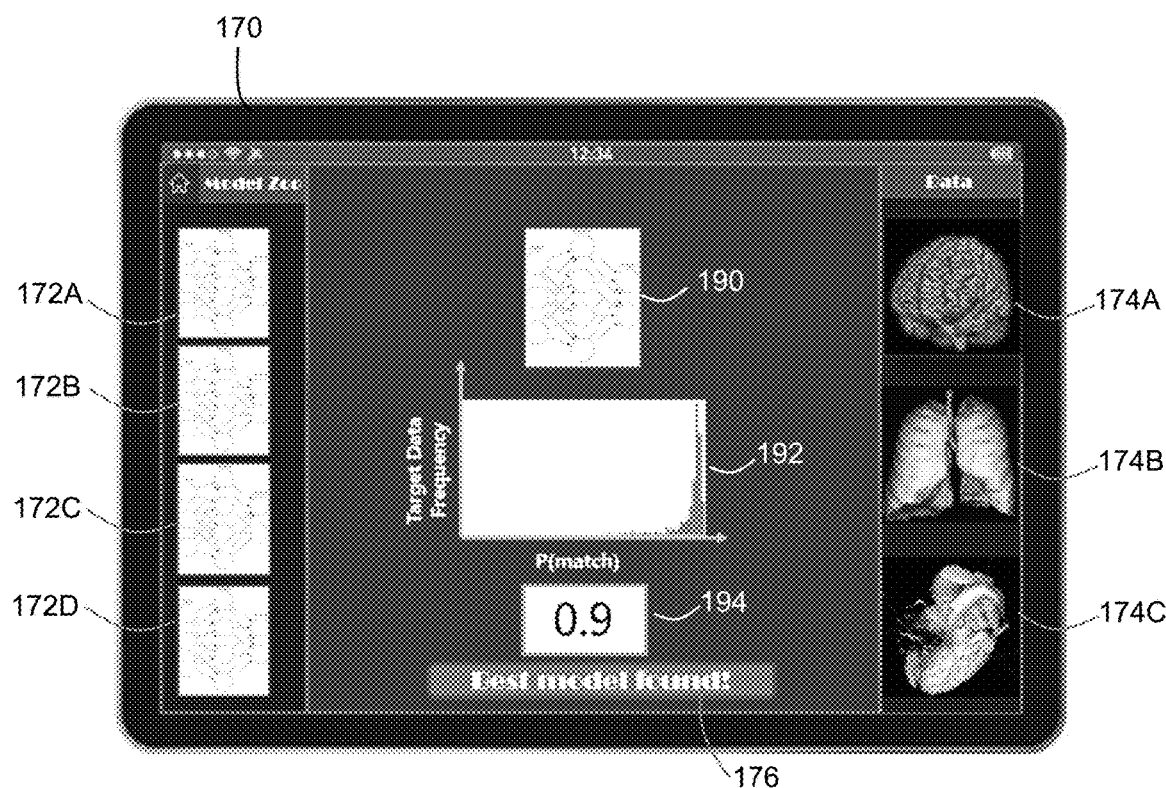
FIG. 15 is a schematic illustration of a model output on the user interface of FIG. 13.

FIGS. 13, 14 and 15 illustrate a user interface 170 which may be presented to a user, for example a clinician or data scientist. The user interface 170 is for use in model selection. In FIGS. 13, 14 and 15, the user interface 170 is presented on a tablet. In other embodiments, the user interface 170 may be presented on any suitable display device 26.

The user interface 170 shows a set of icons representing a plurality of trained models 172A, 172B, 172C, 172D. The models 172A, 172B, 172C, 172D may be trained to perform any appropriate task. For example, the models 172A, 172B, 172C, 172D may be trained classifiers. Only four trained models 172A, 172B, 172C, 172D are illustrated for simplicity. In practice, any number of trained models 172A, 172B, 172C, 172D may be available for use.

The user interface 170 also shows icons representing a set of anatomical regions. In the example shown in FIGS. 13, 14 and 15, the anatomical regions are the brain 174A, lungs 174B and heart 174C.

The user interface 170 also includes a button 176. At the start of a user interaction process as illustrated in FIG. 13, the button 176 displays the text 'Find best model'.

FIG. 14 illustrates a user's interaction with the user interface 170. The user 170 taps on the user interface 170 to select one of the icons representing an anatomical region. In the example shown in FIG. 14, the user selects the brain 174A. FIG. 14 represents the user's action by a hand image 180.

In response to the user's selection of the brain, the model selection circuitry 38 inputs data into each of the models 172A, 172B, 172C, 174D, the data comprising brain images.

The model selection circuitry 38 inputs the model activations produced by the brain images to a trained metalearner 70 to determine an aggregated P(match) value for each of the models 172A, 172B, 172C, 174D, for example using a method as described above with reference to FIG. 7.

The model selection circuitry 38 selects the one of the models 172A, 172B, 172C, 174D having the highest aggregated P(match) value. The model selection circuitry 38 displays on the user interface 170 an icon 190 representing the selected model. The model selection circuitry 38 also displays a plot of P(match) values 192 and an aggregated P(match) value 194 for the selected model.

The model selection circuitry 38 changes the text of the button 176 to 'Best model found'.

In other embodiments, the selected model 190 and/or plot 192 and/or aggregated P(match) value may not be displayed to the user. For example, the user may just be informed that a best model has been found. The selected best model may be passed internally to the classification circuitry 39 or to another circuitry or apparatus. The selected best model may be used to perform any appropriate task.

In the embodiment described above with reference to FIGS. 13, 14 and 15, the best model is selected for use on brain images. In other embodiments, a best model may be selected for use on any suitable anatomy or data set.

Embodiments describes above relate to the selection of models for processing medical image data. In other embodiments, the models may be for the processing of any type of medical data, for example, clinical notes, vital sign data or laboratory data. The models may be for processing data from any human or animal subject or subjects. The models may relate to any suitable anatomy and/or pathology.

In further embodiments, the models may be for the processing of any type of data, which may not be medical data. The models to be compared and selected may be trained to perform any appropriate task or tasks. The metalearner may be trained on any one or more models.

Certain embodiments provide a machine learning model and data sample matching tool, and a method comprising a metalearner trained to map the data sample to the model. The data sample and the model are represented as vectors d and m, where m comprises the model weights. The metalearner is trained by classifying the institution that the data sample d came from as the same institution (match) or a different institution (mismatch) as the model. The metalearner training also incorporates the accuracy of the model m on the data sample d so as to downweight samples where the model match does not correlate with the model performance. The metalearner has a number of outputs, at intermediate levels in the model, and the result is a combination of the outputs e.g. weighted average. If the model is a convolutional neural network, the metalearner may also learn from intermediate spatial/sequential representations in the network (activations a (from within d) across pixels/voxels, i.e. feature maps.

The metalearner may be used to select one or multiple models (i.e. ensemble) to apply to the novel data sample. Multiple novel data samples may be treated as a distribution and summary metrics (e.g. mean) used to select the model (s). The metalearner may be used to detect anomalous data on which the model will not perform well.

The metalearner may be used for the purpose of selecting training data for personalized models in a federated learning setup. The metalearner may be used for the purpose of selecting a pre-trained model in order to fine-tune (adapt). The metalearner may be used for the purpose of selecting a pre-trained model in order to add knowledge (continual learning).

Certain embodiments provide a method of processing medical data comprising: applying a trained model to a target medical data set to generate an output, wherein the model has been trained on a plurality of source data sets; determining a measure of relevance of the source data sets to the target data set; using the determined measure of relevance to determine the suitability of the use of the model for the target data set.

The determining of the measure of relevance may comprise using a further, trained relevance-learning model, that has been trained on data generated by source models being applied to source data sets, wherein the using of the trained relevance-learning model comprises applying the trained relevance-learning model to data generated when the trained relevance-learning model is applied to the target data set, thereby to obtain the measure of relevance.

The applying of the trained model to the target data set may produce intermediate data that is used to generate the output, and the generated data to which the further trained relevance-learning model is applied may include said intermediate data.

The intermediate data may comprise at least one of: model weights for at least one layer of the model; data and model weight pair vectors.

The trained relevance-learning model may be trained using model weights generated by source models applied to source data sets.

The trained relevance-learning model may be trained in a supervised manner to distinguish between source models applied to source data sets for which the source models are more suitable and source models applied to source data sets for which the source models are less suitable.

The suitability may be determined based on similarity of the distribution of the source data and/or based on the origin of the source data on which the source models were trained.

The training of the relevance-learning model may include using a weighting, optionally based on cross-entropy, to weight the importance of at least some of: data-distribution similarity, origin of source data and/or source model, and at least one other property of the source data and/or source models.

The determined measure of relevance may be based on a similarity of data distribution for the data set and for the source data sets on which the model was trained.

The determining of the measure of relevance may comprise using a plurality of further, trained relevance-learning models, that have been trained on data generated by source models being applied to source data sets, wherein different ones of the trained relevance-learning models are trained on different layers of the source models.

The determined measure of relevance may be used to select a model from the plurality of candidate models.

The data set may comprise volumetric medical imaging data. The data set may comprise a set of voxels representing a volume. The output may comprise a segmentation and/or an identification of an anatomical feature or pathology.

Certain embodiments provide a medical system comprising a processing circuitry configured to: receive a first neural network trained by first data set acquired in a first cohort, receive second data set acquired in a second cohort, output affinity-relating value which represents an affinity between data included in the second data set and the first neural network by inputting the data included in the second data set and the first neural network to a second neural network, wherein the second neural network is trained to output affinity-relating value based on predetermined data and a predetermined trained neural network.

The processing circuitry may be further configured to train the second neural network by giving a supervision by inputting the first data set.

The processing circuitry may be further configured to train the second neural network by inputting weights of the first neural network and the values of perceptron of the first neural network when inputted a predetermined data to the first neural network.

The processing circuitry may be further configured to output a plurality of affinity-relating values which represents an affinity between data included in the second data set and the first neural network, specify a median value among the plurality of affinity-relating values.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical system comprising:
  processing circuitry configured to:
   receive a plurality of candidate first trained models, wherein the plurality of candidate first trained models have each been trained using a first data set acquired in a first cohort;
   receive a second data set acquired in a second cohort;
   train a second model to produce a second trained model to output affinity-relating values which represent affinity between data and an input candidate first trained model;
   for each of the plurality of candidate first trained models:
    apply a set of weights of the respective candidate first trained model to a plurality of data samples of the second data set to obtain a respective set of activation values for each of the data samples;
    apply the second trained model to data included in the second data set, the activation values obtained by applying the set of weights of the candidate first trained model to the data samples of the second data set, and data representative of the set of weights of the respective candidate first trained model to obtain a respective affinity-relating value which represents an affinity between the data included in the second data set and the respective candidate first trained model; and
   select at least one candidate first trained model from the plurality of candidate first trained models based on the respective affinity-relating values.

2. The medical system according to claim 1, wherein the affinity-relating value represents or is dependent on an affinity between the data included in the second data set and data included in the first data set.

3. The medical system according to claim 1, wherein the training comprises, for each data sample of a set of training data, inputting to the second model a set of weights for the first trained model and a set of activation values for the first trained model, wherein the activation values are obtained by inputting the data sample to the first trained model.

4. The medical system according to claim 1, wherein the first trained model comprises a first neural network and/or the second trained model comprises a second neural network.

5. The medical system according to claim 1, wherein the processing circuitry is configured to output a plurality of affinity-relating values which represent an affinity between data included in the second data set and the first trained model, and wherein the processing circuitry is configured to determine an aggregated value from the affinity-relating values.

6. The medical system according to claim 5, wherein the aggregated value comprises a median of the affinity-relating values.

7. The medical system according to claim 1, wherein the processing circuitry is configured to use the affinity-relating value to determine a suitability of use of the selected at least one candidate first trained model for the second data set.

8. The medical system according to claim 1, wherein the processing circuitry is further configured to input data included in the second data set and data representative of the first trained model into further second trained models, wherein the further second trained models are trained on different layers of the first trained model.

9. The medical system according to claim 1, wherein the training comprises supervised learning using at least part of the first data set and the first trained model.

10. The medical system according to claim 1, wherein the first trained model is trained to output a classification and/or a segmentation and/or an identification of an anatomical feature or pathology.

11. The medical system according to claim 1, wherein the first data set and second data set each comprise volumetric medical imaging data.

12. The medical system according to claim 1, wherein the training of the second trained model comprises using a loss function which compares the affinity-relating values output by the second trained model with ground truth information.

13. The medical system according to claim 12, wherein the loss function comprises a cross-entropy.

14. The medical system according to claim 12, wherein the loss function is weighted by an accuracy of the input trained model that is input to the second model.

15. A method comprising:
receiving a plurality of candidate first trained models, wherein the plurality of candidate first trained models have each been trained using a first data set acquired in a first cohort;
receiving a second data set acquired in a second cohort;
training a second model to produce a second trained model to output affinity-relating values which represent affinity between data and an input candidate first trained model;
for each of the plurality of candidate first trained models:
applying a set of weights of the respective candidate first trained model to a plurality of data samples of the second data set to obtain a respective set of activation values for each of the data samples;
applying the second trained model to data included in the second data set, the activation values obtained by applying the set of weights of the candidate first trained model to the data samples of the second data set, and data representative of the set of weights of the respective candidate first trained model to obtain a respective affinity-relating value which represents an affinity between the data included in the second data set and the respective candidate first trained model; and
selecting at least one candidate first trained model from the plurality of candidate first trained models based on the respective affinity-relating values.

16. A medical system comprising:
processing circuitry configured to train a second model to output affinity-relating values which represent affinity between data samples of a data set and at least one first trained model, the training comprising:
receiving training data comprising a plurality of data samples, a respective set of weights of each of a plurality of first trained models, and activation values obtained by applying the respective set of weights of each of the plurality of first trained models to the training data; and
using the training data, the data representative of the weights of the plurality of first trained models and the activation values for training the second model to output affinity-relating values.

17. A method comprising:
training a second model to output affinity-relating values which represent affinity between data samples of a data set and at least one first trained model, the training comprising:
receiving training data comprising a plurality of data samples, a respective set of weights of each of a plurality of first trained models, and activation values obtained by applying the respective set of weights of each of the plurality of first trained models to the training data; and
using the training data, the data representative of the weights of the plurality of first trained models and the activation values for training the second model to output affinity-relating values.

* * * * *